US006549856B2

United States Patent
Baker

(10) Patent No.: US 6,549,856 B2
(45) Date of Patent: Apr. 15, 2003

(54) FLUID CONTAMINANT SENSOR

(75) Inventor: Michael Charles Baker, Gretton (GB)

(73) Assignee: Moog Inc., East Aurora, NY (US)

( * ) Notice: Subject to any disclaimer, the term of this patent is extended or adjusted under 35 U.S.C. 154(b) by 0 days.

(21) Appl. No.: 09/910,598

(22) Filed: Jul. 20, 2001

(65) Prior Publication Data

US 2002/0035436 A1 Mar. 21, 2002

(30) Foreign Application Priority Data

Jul. 21, 2000 (GB) .............................................. 0017987

(51) Int. Cl.[7] .............................................. G06F 19/00
(52) U.S. Cl. .......................... 702/50; 702/25; 702/114; 73/61.73; 73/61.41
(58) Field of Search ............................. 73/61.73, 53.05, 73/53.07, 61.41, 61.42, 61.64, 61.68; 702/50, 25, 114

(56) References Cited

U.S. PATENT DOCUMENTS

| 4,495,799 A | * | 1/1985 | Fisher et al. ................ 73/61.73 |
| 4,583,396 A | * | 4/1986 | Hunt et al. ................. 73/61.73 |
| 5,095,740 A | * | 3/1992 | Hodgson et al. ............ 210/340 |
| 6,474,144 B1 | * | 11/2002 | Barnes et al. ............... 73/61.71 |

FOREIGN PATENT DOCUMENTS

GB  2348543  * 4/2000  .......... G01N/15/06

* cited by examiner

Primary Examiner—John Barlow
Assistant Examiner—Stephen J. Cherry
(74) Attorney, Agent, or Firm—Phillips, Lytle, Hitchcock, Blaine & Huber LLP

(57) ABSTRACT

The invention provides an improvement in apparatus (20) for testing the level of contaminants in a fluid during a test period. The apparatus has a source of pressurized fluid ($P_s$) to be tested; a fluid sump (R); and a test passage (48) which is substantially free of occluding contaminants at the beginning of the test period and which is adapted to be supplied with a flow of fluid from the source. The passage is so configured and arranged as to be progressively occluded by contaminants in the fluid flow. The apparatus also includes a device (23) defining a variable-volume chamber (47). The volume of said chamber is variable between a minimum value and a maximum value. The improvement comprises: a valve (36) operatively arranged to direct fluid that has passed through the test passage to the chamber when it is desired to expand the volume of the chamber, and arranged to direct fluid that has passed through the test passage to the sump and to permit fluid in said chamber to flow to the sump when it is desired to contract the volume of said chamber; a return mechanism (24) for selectively urging the chamber to contract; a calibrated sensor (44) for measuring the volume of the chamber; a controller (50) for operating the valve and return mechanism to cause the chamber to repeatedly expand and contract cyclically during said test period; and timer (53) for measuring the time required for the fluid flow through the test passage to cause the chamber to increase from a first volume to a second volume. The flow through the test passage during each of the successive cycles of the chamber may be calculated.

14 Claims, 1 Drawing Sheet

FLUID CONTAMINANT SENSOR

TECHNICAL FIELD

The present invention relates generally to fluid-powered systems, and, more particularly, to an improved sensor for determining the level of particulate contaminants in a system fluid.

BACKGROUND ART

Contaminated fluids can cause erratic operation or catastrophic failure of pumps, valves and actuators used in hydraulic control systems. Many aircraft fuel systems use servo-based technology, and contamination can lead to dangerous failures. This is often exacerbated by the fact that these are typically "total loss" failures.

Fluid cleanliness is difficult to monitor. Lubricating oil systems for high-value plant and machinery, such as gas and steam turbines, must be maintained to an exceptionally high standard if major damage and loss of production is to be avoided. Traditional ways of monitoring oil cleanliness are inconvenient and expensive, and often the results are only available after considerable delay.

The contamination sensitivity of various elements of a fluid power system is fairly well established. For pumps and motors, there is a critical range of particulate size which will cause most damage. However, a servovalve can experience erratic operation and accelerated wear due to particles as small as a few microns impacting on, and accumulating around, the lands of a valve spool. These potential failure modes are addressed and guarded against by specific design features that are built into the servovalve. The same is true of the other components within the system. However, experience has shown that there is still a strong correlation between the cleanliness of the fluid and the reliability of the system in which it is used.

Advances in fluids, filtration and component design have resulted in improvements. As a result, stable hydraulic systems are generally reliable, but problems arise when parameters change. For example, a pump might fail, sending a cloud of debris through the system. The fluid may overheat and create a multitude of tiny hard particles, New lubricating oil, added to the tank might not be quite as clean as was thought. Fuel oil (e.g., aircraft fuel) does not re-circulate through the system, so there is not the opportunity for it to sequentially pass through various filters. Such occurrences can wreak havoc with even a well-designed system, and, being unexpected and random in nature, can jeopardize both plant and safety in an unpredictable manner.

Traditionally, cleanliness has been monitored by taking a sample of the fluid, and then assessing the number and size of contaminant particles in such sample. This can be done either manually (e.g., by using a microscope) or automatically (e.g., usually employing some sort of light-blockage technique). Both techniques are essentially laboratory procedures. Although it is true that most of these instruments are portable, and, in some cases, can even be connected directly to the fluid system to be tested, none is regarded as being small or robust enough to be permanently installed.

Accordingly, there is believed to be a need for a contaminant sensor which is small, robust and suitable for permanent installation in high-value and/or safety-critical equipment. A system potentially offering these features has been developed by others (see, e.g., published British Pat. Application No. 2,361,548), but o g to the necessary size of the flow-measuring piston required, it is still awkwardly large. The inventive device presented herein provides a novel technique which permits the piston size to be dramatically reduced.

DISCLOSURE OF THE INVENTION

With parenthetical reference to the corresponding parts, portions or surfaces of the disclosed embodiment, merely for purposes of illustration and not by way of limitation, the present invention provides an improvement in apparatus (20) for testing the level of contaminants in a fluid during a test period.

The apparatus has a source of pressurized fluid ($P_s$) to be tested; a sump (R); a test passage (48) which is substantially free of occluding contaminants at the beginning of the test period and which is adapted to be supplied with a flow of fluid from the source, the passage being so configured and arranged as to be progressively occluded by contaminants in the fluid flow; and a device defining a variable-volume chamber (47), the volume of the chamber being variable between a minimum value and a maximum value. The improvement broadly comprises a valve (36) operatively arranged to direct fluid that has passed trough the test passage (48) to the chamber (47) when it is desired to expand the volume of the chamber, and arranged to direct fluid that has passed through the test passage to the sump, and to permit fluid in the chamber to flow to the sump, when it is desired to contract the volume of the chamber, a return mechanism (24) for selectively urging the chamber to contract, a calibrated sensor (44) for measuring the volume of the chamber; a controller (50) for operating the flush and recycle valves to selectively cause the chamber to repeatedly expand and contract cyclically during the test period; and a timer (53) for measuring the time required for the fluid flow through the test passage to cause the chamber to increase from a first volume to a second volume; whereby the flow through the test passage during each of the successive cycles of chamber volume may be calculated.

The level of contamination in the fluid may be determined as a function of the flow through the test passage during the first cycle and the number of cycles required for such flow to be reduced to a predetermined minimum value. The test passage may have an annular transverse crossection, such as defined between the facing surfaces on a valve spool land and a cylindrical bushing (not shown) mounted on the body. The device may have a piston (39) mounted for sealed sliding movement within a cylinder (40). The valve (36) may be a relief valve. The return mechanism may be fluid powered, and the controller may cause the chamber to expand or contract cyclically as a function of the flow through the passage.

Accordingly, the general object of the invention is to provide a fluid contaminant sensor. Another object is to provide an improved fluid contaminant sensor which is adapted to be mounted on, or otherwise permanently associated with, the system in which the fluid is contained.

Still another object is to provide a fluid contaminant sensor which closely simulates the passages that are likely to be encountered in the accompanying fluid system, and which is able to simulate and predict the effect of such contaminants on flow through the system.

These and other objects and advantages will become apparent from the foregoing and ongoing written specification, the drawings, and the appended claims.

DESCRIPTION OF THE PREFERRED EMBODIMENTS

Figure 1:
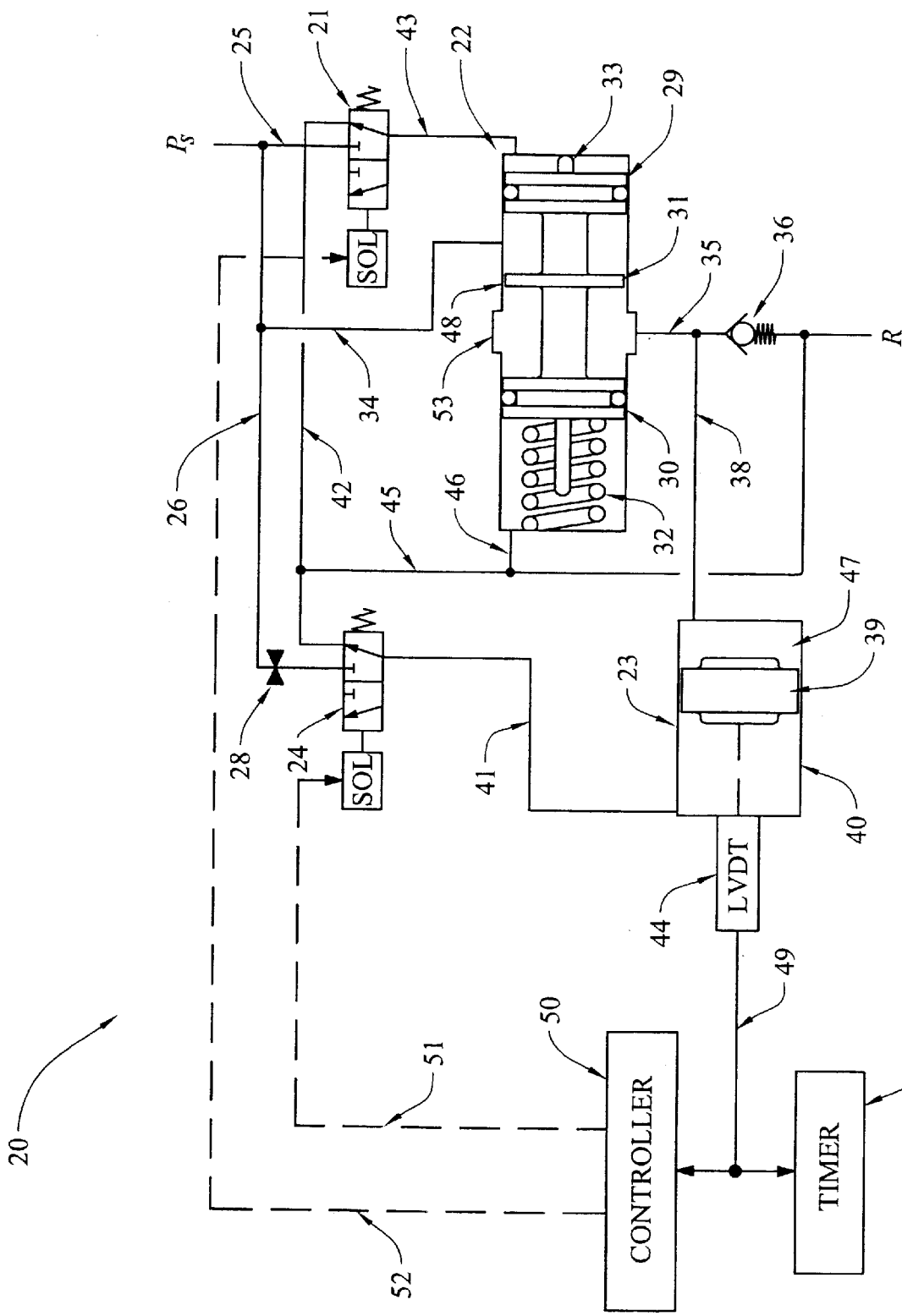
FIG. 1 is a schematic block diagram of a fluid contaminant sensor, this view showing the contaminant-sensing spool valve, the flow-measuring piston, the recycling valve and the flush valve.

At the outset, it should be clearly understood that like reference numerals are intended to identify the same structural elements, portions or surfaces consistently in the drawing figure, as such elements, portions or surfaces may be further described or explained by the entire written specification, of which this detailed description is an integral part. Unless otherwise indicated, the drawings are intended to be read (eg., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis or elongation, or axis of rotation, as appropriate.

Referring now to the drawings, and more particularly to FIG. 1 thereof an improved fluid contaminant sensor is generally indicated at 20. Sensor 20 is shown as broadly including a solenoid-operated flush valve 21, a contaminant-sensing spool valve 22, a flow-measuring piston-and-cylinder assembly 23, and a recycle valve 24. Pressurized fluid, containing an unknown quantity of contaminants, from a suitable source is supplied to the system as supply pressure $P_s$. Supply pressure is provided via line 25 to flush valve 21, and via line 26 to recycle valve 24. Line 26 is shown as having a restricted orifice 28 therein. Flush valve 21 and recycle valve 24 are both electrically-operated two-position solenoid-type valves, and are schematically shown as being de-energized in FIG. 1.

Contaminant sensing valve 22 is shown as having a valve spool mounted for sealed sliding movement within a body. This valve has a rightward sealed land 29, a leftward sealed land 30, and an intermediate non-sealed silting land 31 arranged in closely-spaced facing relation to an inwardly-facing cylindrical body or bushing surface. A spring 32 is operatively arranged in the spool left end chamber, and acts between the body and the valve spool. This spring continuously urges the valve spool to move rightwardly relative to the body until a nub 33, extending rightwardly from the spool right end face, abuts the leftwardly-facing end wall of the right end chamber.

Supply pressure $P_s$ in line 26 is also provided via line 34 to the annular space of the contaminant-sensing valve between intermediate silting land 31 and right land 29. Contaminated fluid from the source may then flow through the annular orifice 48 defined between silting land 31 and the facing body surface into the annular chamber between silting land 31 and left land 30. This chamber communicates with a fluid sump at return pressure R via a conduit 35, which contains a relief valve 36. Fluid in line 35 is supplied via line 38 to the right end chamber 47 of the flow-measuring piston-and-cylinder assembly 23. This assembly includes a piston 39 mounted for sealed sliding movement within a cylinder 40. The left end chamber of piston and cylinder assembly 23 communicates via line 41 with recycle valve 24, which in turn communicates via line 42 with flush valve 21. Line 43 communicates flush valve 21 with the spool right end chamber of contaminant-sensing valve 22. Line 42 communicates with the fluid return R via lines 45 and 35. Line 46 communicates the spool left end chamber of the contaminant-sensing valve with line 45.

The position of piston 39 relative to cylinder 40 is continually monitored by a position sensing device, such as a linear variable differential transformer ("LVDT") 44.

The operation of the improved device will now be described.

Assume first that recycle valve 24 and flush valve 21 are both de-energized, as shown, such that flow from $P_s$ past these valves will be blocked. In this condition, pressurized contaminated fluid from the source $P_s$ will flow via lines 26 and 34 to the annular chamber to the right of silting land 31 in the contaminant-sensing valve, and then through the annular test passageway 48 to the return via relief valve 36. However, relief valve 36 has a spring biasing a ball to a closed position, such that flow through the valve will produce a slightly-elevated back pressure upstream of the valve. Hence, when recycle valve 24 is de-energized such that the left end chamber of flow-measuring valve 23 communicates with return via communicating lines 41, 42 and 45, a differential pressure across piston 39 will cause fluid in line 35 to flow into the flow-measuring cylinder assembly right end chamber 47, rather than flowing to return. The pressure differential across piston 39 drives flow-measuring piston 39 leftwardly. The position of this piston is continuously monitored by LVDT 44, which provides an electrical signal via line 49 to a controller 50. The controller selectively provides output signals to the recycle valve and the flush valve via lines 51 and 52, respectively.

When the flow-measuring piston 39 has been displaced leftwardly toward the end of its stroke, controller 50 energizes the solenoid of the recycle valve to its alternative position. In this condition, supply pressure from the source is applied via now-connected lines 26 and 41 to the left end chamber of the flow-measuring piston. Such pressure will urge the flow-measuring piston to move rightwardly, forcing fluid in the right end chamber 47 out through line 38 and relief valve 36 to the return. This causes the pressure in line 35 to increase to the previously-mentioned slightly-elevated back pressure. Since this back pressure is very small compared to the pressure drop across the test passageway 48, other will not be a significant decrease in the pressure drop across silting land 31. Hence, there will not be a significant change in the flow of contaminated fluid, or the rate of occlusion. Once flow-measuring piston 39 has been sufficiently displaced to the right, controller 50 de-energizes the solenoid of recycling valve 24, allowing the recycle valve to return to the position shown. In this arrangement, fluid passing through the orifice 48 will again flow via conduits 35, 38 to enter chamber 47 and drive the flow-measuring piston leftwardly, forcing fluid in the left end chamber to flow to return via now-connected conduits 41, 42 and 45. Thus, controller 50 may cause the flow-measuring piston to oscillate back and forth, thereby cyclically expanding and contracting the volume of chamber 47. A timer 53 is arranged to continually sense the time of these oscillations. Thus, as the orifice 48 becomes progressively occluded by the presence of contaminants in the fluid, the time required to increase the volume of chamber 47 from a first volume to a second volume will progressively increase. This reflects the diminished flow through the progressively-occluded orifice 48.

The device operates cyclically in this manner until the cycle time indicates that the flow through the orifice 48 has reached a predetrmined minimum value, at which point the test may be stopped and the contamination level calculated from the values of initial flow and final flow and the number of cycles in the test.

The test may be rerun by clearing or flushing the occluded passageway and repeating the test cycles. To accomplish this, the controller sends an appropriate signal to the solenoid of flush valve 21. This causes the flush valve to move to the alterative position, which provides supply pressure via now-communicating lines 25, 43 to the contaminant-sensing valve spool right end chamber. This drives the contaminant-sensing valve spool leftwardly within its body, overcoming the opposing bias of spring 32. By moving silting land 31 to a larger-diameter region 53 of the body, the occlusions caused by the accumulated contaminants from the previous cycle are permitted to be flushed and removed toward the return. Thus, the flush valve operates to substantially remove all contaminants from the orifice 48, and to ready the device for the next series of cyclical flow-measurements.

While the flow through the annular clearance test orifice 48 is dependent on fluid temperature, this effect is essentially eliminated from the calculation of contamination level by basing the calculation on the ratio of the initial value to the final value of the measured flow, rather than on the absolute values of flow, and also by keeping the measuring time relatively short so that the temperature is constant. To reduce this time to a minimum, an alternative test sequence can be set up to determine the final flow time, following which the test orifice is flushed and the test restarted to determine the initial flow time.

Modifications

The present invention contemplates that many modifications may be made. For example, while the apparatus has been shown schematically as including two-position solenoid operated valves, this valving arrangement could readily be changed or modified as desired. The structure and operation of the various components of the improved sensor may be changed or modified as desired. It should be clearly understood that the accompanying drawing is used to illustrate the principle of operation of the improved sensor, without intending to limit the structure that might perform the necessary functions defined by the various claims.

Therefore, while the presently-preferred form of the improved contaminant sensor has been shown and described, and several modifications thereof discussed, persons skilled in this art will readily appreciate that various additional changes and modifications may be made without departing from the spirit of the invention, as defined and differentiated by the following claims.

What is claimed is:

1. In apparatus for testing the level of contaminants in a fluid during a test period, said apparatus having a source of pressurized fluid to be tested; a fluid sump; a test passage which is substantially free of occluding contaminants at the beginning of said test period and which is adapted to be supplied with a flow of fluid from said source, said passage being so configured and arranged as to be progressively occluded by contaminants in said fluid flow; and a device defining a chamber, the volume of said chamber being variable between a minimum value and a maximum value; the improvement which comprises:

a valve having a first state operatively arranged to direct fluid that has passed through said passage to said chamber to expand the volume of said chamber, and having a second state arranged to direct fluid that has passed through said passage to said sump and to permit fluid in said chamber to flow to said sump to contract the volume of said chamber;

a return mechanism for selectively urging said chamber to contract;

a calibrated sensor for measuring the volume of said chamber;

a controller for operating said valve and return mechanism to cause said chamber to repeatedly expand and contract cyclically during said test period; and a timer for measuring the time required for the fluid flow through said test passage to cause said chamber to increase from a first volume to a second volume;

whereby the flow through the test passage during each of the successive cycles of said chamber may be calculated.

2. The improvement as set forth in claim 1 wherein the level of contamination in said fluid may be determined as a function of the calculated value of flow through said test passage during the first cycle and the number of cycles required for such flow to be reduced to a predetermined minimum value.

3. The improvement as set forth in claim 1 wherein the level of contamination in said fluid may be determined as a function of the ratio of the calculated initial value of flow through said test passage during the first cycle to the calculated final value of flow through said test passage during the last of a predetermined number of cycles.

4. The improvement as set forth in claim 3 wherein said initial value of flow is determined by restarting the test sequence immediately following the determination of said final value.

5. The improvement as set forth in claim 1 wherein said test passage has an annular transverse cross-section.

6. The improvement as set forth in claim 1 wherein said device has a piston mounted for sealed sliding movement relative to a cylinder.

7. The improvement as set forth in claim 1 wherein said valve is a relief valve.

8. The improvement as set forth in claim 1 wherein said return mechanism is fluid powered.

9. The improvement as set forth in claim 1 wherein said controller causes said chamber to expand and contract cyclically as a function of the flow through said passage.

10. The improvement as set forth in claim 1 wherein said test passage is flushed of contaminants before the beginning of said test period.

11. The improvement as set forth in claim 4 wherein said apparatus is operated to direct fluid that has passed through said test passage to said chamber to determine initial and final flow values, and wherein the level of contamination in said fluid is determined as a function of the ratio of said initial and final flow values.

12. The improvement as set forth in claim 1 wherein said apparatus is operated sequentially to direct said fluid into said chamber to determine an initial flow value, to direct said fluid to said sump for a predetermined period of time, and to thereafter again direct said fluid into said chamber to determine a second flow value, and wherein the level of contamination in said fluid is determined as a function of the ratio of said initial and second flow values.

13. The method of testing the level of contaminants in a fluid during a test period using apparatus having a source of pressurized fluid to be tested; a fluid sump; a test passage that is substantially free of occluding contaminants at the beginning of said test period and which is adapted to be supplied with a flow of fluid from said source, said passage being so configured and arranged as to be progressively occluded by contaminants in said fluid flow; and a device defining a chamber, the volume of said chamber being variable between a minimum value and a maximum value; said method comprising the steps of:

(a) passing contaminated fluid continuously though said test passage during said test period;

(b) directing said flow through said test passage to said chamber to increase the volume of same;

(c) measuring the time rate of change of volume of said chamber as said chamber expands to provide a first flow-measurement;

(d) redirecting said flow through said test passage to said sump;

(e) reducing the volume of said chamber; and (f) repeating steps (b)–(e) at least one time during said test period to provide at least one successive flow measurement as said test passage becomes progressively occluded during said test period;

thereby to determine the level of contaminants in said fluid as a function of said flow measurements.

14. The method as set forth in claim 13 wherein the level of contaminants in said fluid is determined as a function of the ratio of two flow measurements during said test period.

* * * * *